US010828468B2

(12) United States Patent
Selkee

(10) Patent No.: US 10,828,468 B2
(45) Date of Patent: *Nov. 10, 2020

(54) MEDICAL DEVICE CONTROL HANDLE

(71) Applicant: Biosense Webster (Israel) Ltd., Yokneam (IL)

(72) Inventor: Thomas V. Selkee, Claremont, CA (US)

(73) Assignee: BIOSENSE WEBSTER (ISRAEL) LTD., Yokneam (IL)

(*) Notice: Subject to any disclaimer, the term of this patent is extended or adjusted under 35 U.S.C. 154(b) by 1361 days.

This patent is subject to a terminal disclaimer.

(21) Appl. No.: 14/945,258

(22) Filed: Nov. 18, 2015

(65) Prior Publication Data
US 2016/0067457 A1 Mar. 10, 2016

Related U.S. Application Data

(63) Continuation of application No. 13/300,411, filed on Nov. 18, 2011, now Pat. No. 9,199,061.

(51) Int. Cl.
A61M 25/01 (2006.01)
A61M 25/09 (2006.01)
(Continued)

(52) U.S. Cl.
CPC ........ A61M 25/09 (2013.01); A61M 25/0136 (2013.01); A61M 25/0147 (2013.01);
(Continued)

(58) Field of Classification Search
CPC .. A61B 2018/0091; A61B 2018/00952; A61B 2017/00318; A61B 2017/003
See application file for complete search history.

(56) References Cited

U.S. PATENT DOCUMENTS 5,195,968 A 3/1993 Lundquist et al.
RE34,502 E 1/1994 Webster, Jr.
(Continued)

FOREIGN PATENT DOCUMENTS

CN 101708130 A 5/2010
EP 2165730 A1 3/2010
(Continued)

OTHER PUBLICATIONS

EPO Extended European Search Report dated Feb. 1, 2013 for EP Application No. 12193031.7, 5 pages.

Primary Examiner — Nathan R Price
Assistant Examiner — Weng Lee
(74) Attorney, Agent, or Firm — Etan S. Chatlynne; Roberts Calderon Safran & Cole P.C.

(57) ABSTRACT

A medical device control handle has with a distal component which is adjustable by an actuator assembly by means of a puller member or wire. The actuator assembly includes a user interface rotational dial, a detent tab washer and a spool, where the dial is rotationally coupled to the detent tab washer which transmits rotational movement of the dial to the spool. The spool has a shaft body and a drum end onto which an proximal end portion of the puller member can be wound to manipulate or adjust the distal component. Rotational movement of the detent washer is limited to prevent overrotation and breakage of the puller member. At least one washer is mounted on the shaft body of the spool to help apply compression load on the actuator assembly in friction-inducing contact with one or more components of the actuator assembly.

20 Claims, 12 Drawing Sheets

(51) Int. Cl.
*A61B 18/14* (2006.01)
*A61B 17/00* (2006.01)
*A61B 18/00* (2006.01)

(52) U.S. Cl.
CPC ..... *A61B 18/1492* (2013.01); *A61B 2017/003* (2013.01); *A61B 2017/00323* (2013.01); *A61B 2017/00327* (2013.01); *A61B 2018/0091* (2013.01); *A61B 2018/00839* (2013.01); *A61B 2018/1435* (2013.01); *A61M 2025/09116* (2013.01)

(56) References Cited

U.S. PATENT DOCUMENTS

| | | | |
|---|---|---|---|
| 5,325,845 | A | 7/1994 | Adair |
| 5,363,861 | A | 11/1994 | Edwards et al. |
| 5,462,527 | A | 10/1995 | Stevens-Wright et al. |
| 5,507,717 | A * | 4/1996 | Kura ................... A61B 1/0052 600/146 |
| 5,667,476 | A | 9/1997 | Frassica et al. |
| 5,904,667 | A | 5/1999 | Falwell |
| 6,126,633 | A | 10/2000 | Kaji et al. |
| 6,533,783 | B1 | 3/2003 | Tollner |
| 6,652,506 | B2 | 11/2003 | Bowe et al. |
| 6,899,673 | B2 | 5/2005 | Ogura et al. |
| 7,285,108 | B2 | 10/2007 | Koerner et al. |
| 7,377,906 | B2 | 5/2008 | Selkee |
| 7,491,166 | B2 | 2/2009 | Ueno et al. |
| 2004/0049207 | A1* | 3/2004 | Goldfarb ................. A61F 2/246 606/139 |
| 2005/0288656 | A1* | 12/2005 | Koerner ............ A61M 25/0043 606/21 |
| 2013/0204096 | A1 | 8/2013 | Ku et al. |
| 2014/0200560 | A1 | 7/2014 | Lavender |

FOREIGN PATENT DOCUMENTS

| | | |
|---|---|---|
| JP | 2010069299 A | 4/2010 |
| JP | 2011045720 A | 3/2011 |
| RU | 2033108 C1 | 4/1995 |
| WO | 2008031103 A2 | 3/2008 |

\* cited by examiner

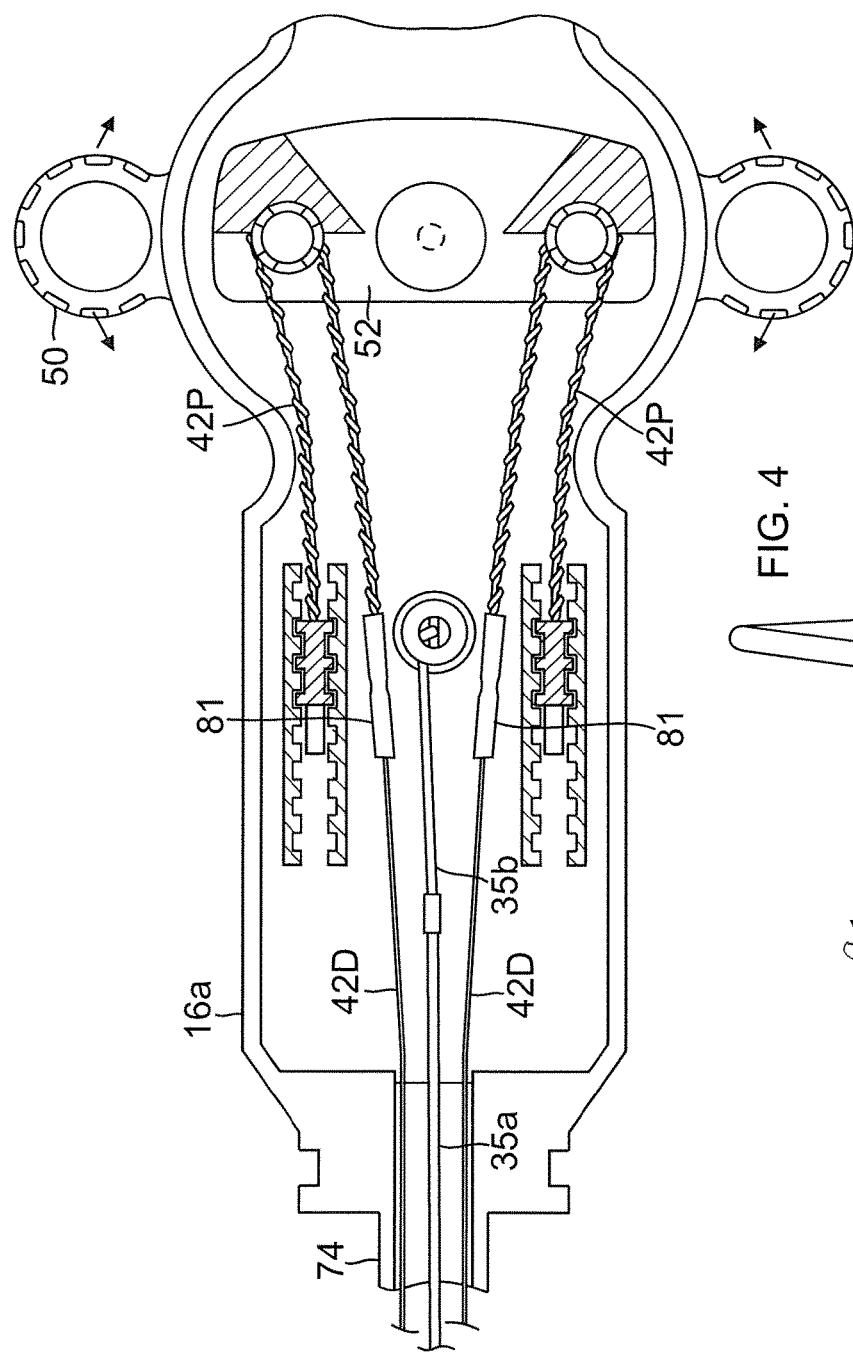
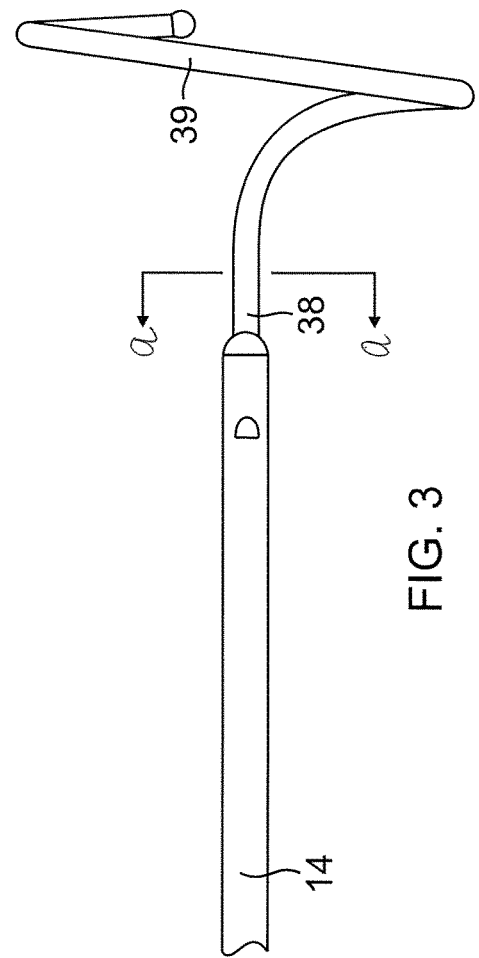
FIG. 3
FIG. 4

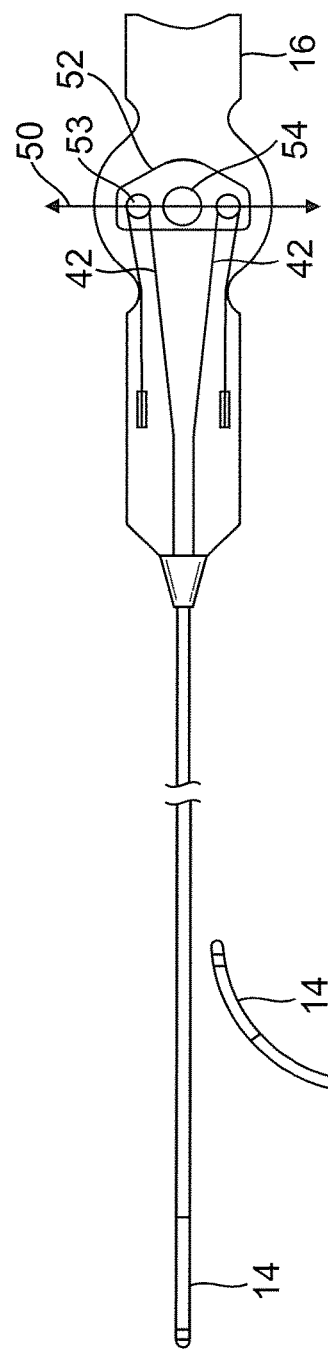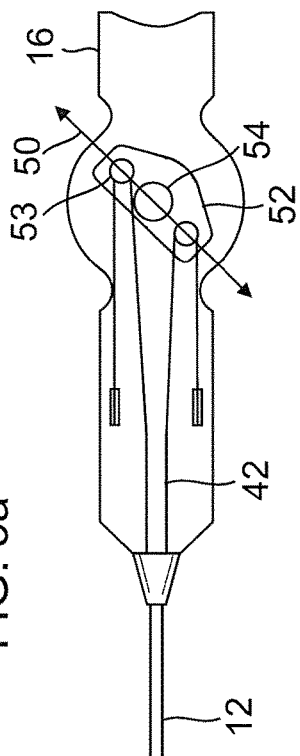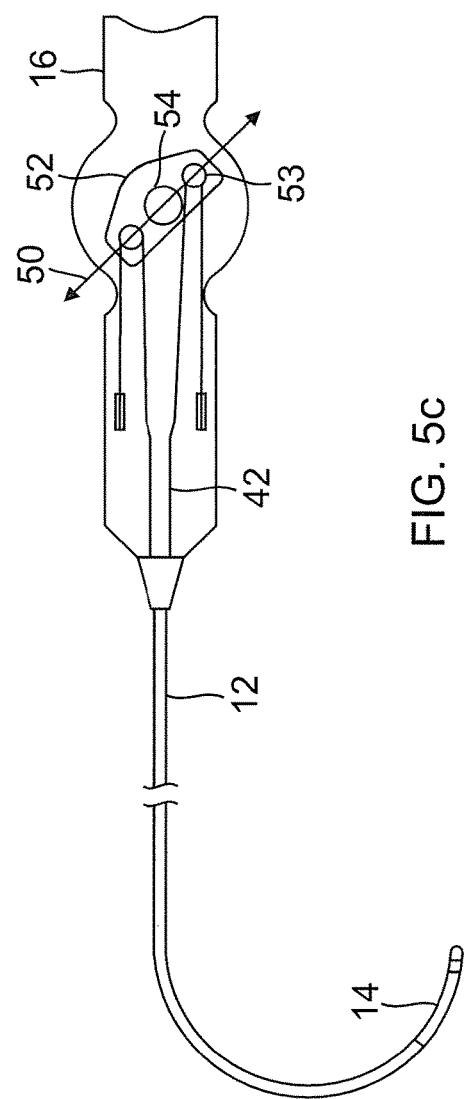
FIG. 5a
FIG. 5b
FIG. 5c

MEDICAL DEVICE CONTROL HANDLE

CROSS-REFERENCE TO RELATED APPLICATION

This application is a continuation of and claims priority to and the benefit of U.S. patent application Ser. No. 13/300,411 filed Nov. 18, 2011, issued as U.S. Pat. No. 9,199,061, the entire content of which is incorporated herein by reference.

FIELD OF INVENTION

This invention relates to a control handle for medical devices, in particular, a control handle having mechanisms for controlling multiple puller wires in separately manipulating different features of a medical device.

BACKGROUND

Electrode catheters have been in common use in medical practice for many years. They are used to stimulate and map electrical activity in the heart and to ablate sites of aberrant electrical activity. Atrial fibrillation is a common sustained cardiac arrhythmia and a major cause of stroke. This condition is perpetuated by reentrant wavelets propagating in an abnormal atrial-tissue substrate. Various approaches have been developed to interrupt wavelets, including surgical or catheter-mediated atriotomy. Prior to treating the condition, one has to first determine the location of the wavelets. Various techniques have been proposed for making such a determination, including the use of catheters with a mapping assembly that is adapted to measure activity within a pulmonary vein, coronary sinus or other tubular structure about the inner circumference of the structure. One such mapping assembly has a tubular structure comprising a generally circular main region generally transverse and distal to the catheter body and having an outer circumference and a generally straight distal region distal to the main region. The tubular structure comprises a non-conductive cover over at least the main region of the mapping assembly. A support member having shape-memory is disposed within at least the main region of the mapping assembly. A plurality of electrode pairs, each comprising two ring electrodes, are carried by the generally circular main region of the mapping assembly.

In use, the electrode catheter is inserted into a guiding sheath which has been positioned a major vein or artery, e.g., femoral artery, and guided into a chamber of the heart. Within the chamber, the catheter is extended past a distal end of the guiding sheath to expose the mapping assembly. The catheter is maneuvered through movements that include deflection of a distal portion of the catheter so that the mapping assembly is positioned at the tubular region in the heart chamber. The ability to control the exact position and orientation of the catheter and also the configuration of the mapping assembly is critical and largely determines how useful the catheter is.

Steerable catheters are generally well-known. For example, U.S. Pat. No. Re 34,502 describes a catheter having a control handle comprising a housing having a piston chamber at its distal end. A piston is mounted in the piston chamber and is afforded lengthwise movement. The proximal end of the elongated catheter body is attached to the piston. A puller wire is attached to the housing and extends through the piston, through the catheter body, and into a tip section at the distal end of the catheter body. The distal end of the puller wire is anchored in the tip section of the catheter. In this arrangement, lengthwise movement of the piston relative to the housing results in deflection of the catheter tip section.

The design described in U.S. Pat. No. RE 34,502 is generally limited to a catheter having a single puller wire. If bi-directional deflection is desire, more than one puller wire becomes necessary. Moreover, if more control is desired, such as contraction of the mapping assembly, an additional puller wire is needed. Furthermore, it is desirable that the mechanism for actuating the additional puller wire be self-holding such that the mechanism can maintain the contraction of the mapping assembly without the need for continuous control by the user. Accordingly, a need exists for a control handle capable of moving a third puller wire that can be used in a hands-free manner.

SUMMARY OF THE INVENTION

The present invention is directed to a medical device control handle with a distal component which is adjustable by an actuator assembly by means of a puller member or wire. In one embodiment, the actuator assembly includes a user interface rotational dial, a detent tab washer and a spool, where the dial is rotationally coupled to the detent tab washer which transmits rotational movement of the dial to the spool. The spool has a shaft body and a drum end onto which an proximal end portion of the puller member can be wound to manipulate or adjust the distal component. Rotational movement of the detent washer is limited so that a user is prevented from over-rotating the dial and breaking or otherwise damaging the puller member. Moreover, at least one washer is mounted on the shaft body of the spool to help apply compression load on the actuator assembly in friction-inducing contact with one or more components of the actuator assembly. To that end, washers include those rotationally coupled to the spool, and those that are either independently rotational (that is, not strictly rotationally coupled to another element) or those that are locked against rotation relative to the spool.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIG. 3 is a side view of an embodiment of a distal assembly.

FIG. 4 is a top plan view of an embodiment of a control handle housing half.

FIG. 5A-5C are schematic top plan views of the control handle housing half in neutral and deflected configurations.

DETAILED DESCRIPTION OF THE INVENTION

The present invention is directed to a medical device control handle. As medical devices, especially, electrophysiology catheters, become more complex with more components to actuate, a control handle should provide independent control of multiple puller wires. The control handle of the present invention utilizes a first actuation member for actuating at least one puller wire in one manipulation of a medical device, including uni-directional deflection, if not a pair of puller wires for bi-directional deflection of a catheter, and a second actuation member for actuating an additional puller wire in another manipulation of the medical device.

Figure 1:
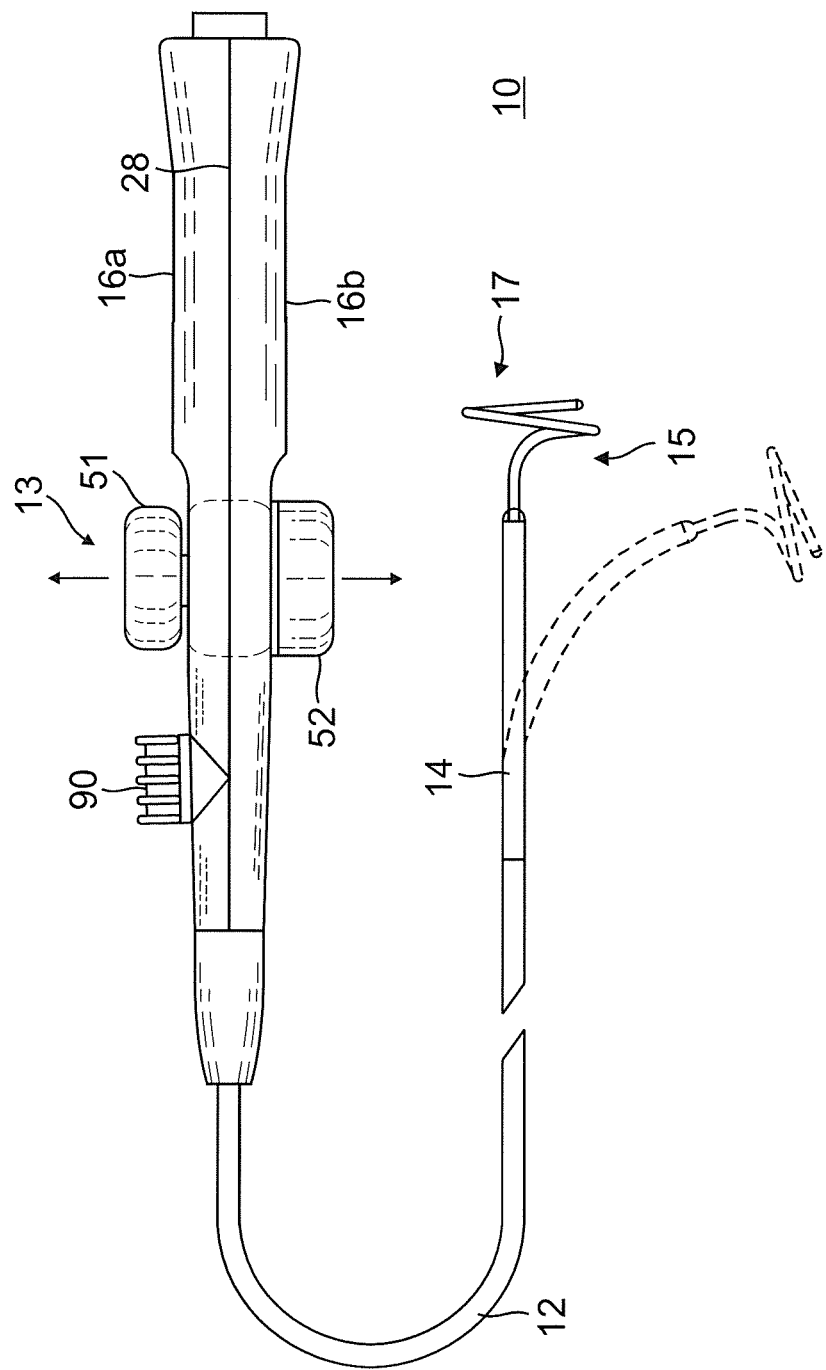
FIG. 1 is a top plan view of one embodiment of the catheter of the present invention.

The catheter of FIG. 1 comprises an elongated catheter body 12, a deflectable intermediate section 14 at a distal end of the catheter body 12, and a tip section 15 including a distal assembly 17 having, for example, a helical form, at a distal end of the intermediate section 14. A control handle 16 for use with the catheter has a deflection dial 50 that is configured to actuate a pair of puller members or wires extending from the control handle 16 and through the catheter body 12 and intermediate section 14 for bi-directional deflection of the intermediate section. In accordance with a feature of the present invention, the control handle further includes an actuator assembly adapted to control a third puller member or wire in manipulating or adjusting the distal assembly 17, for example, to contract the helical form of the distal assembly.

Figure 2A:
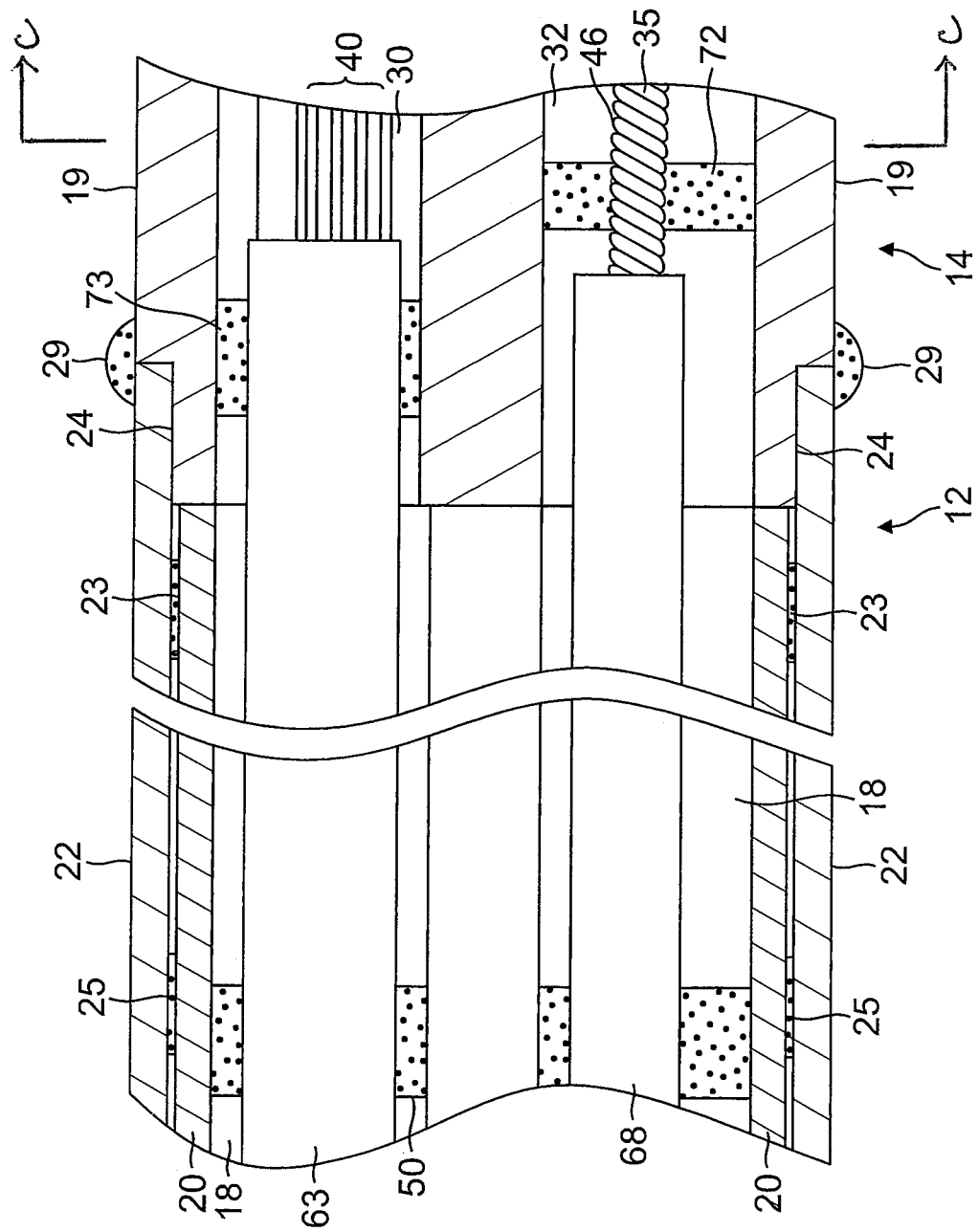
FIG. 2A is a side cross-sectional view of an embodiment of a junction of a catheter body and an intermediate section, taken along a first diameter.
Figure 2B:
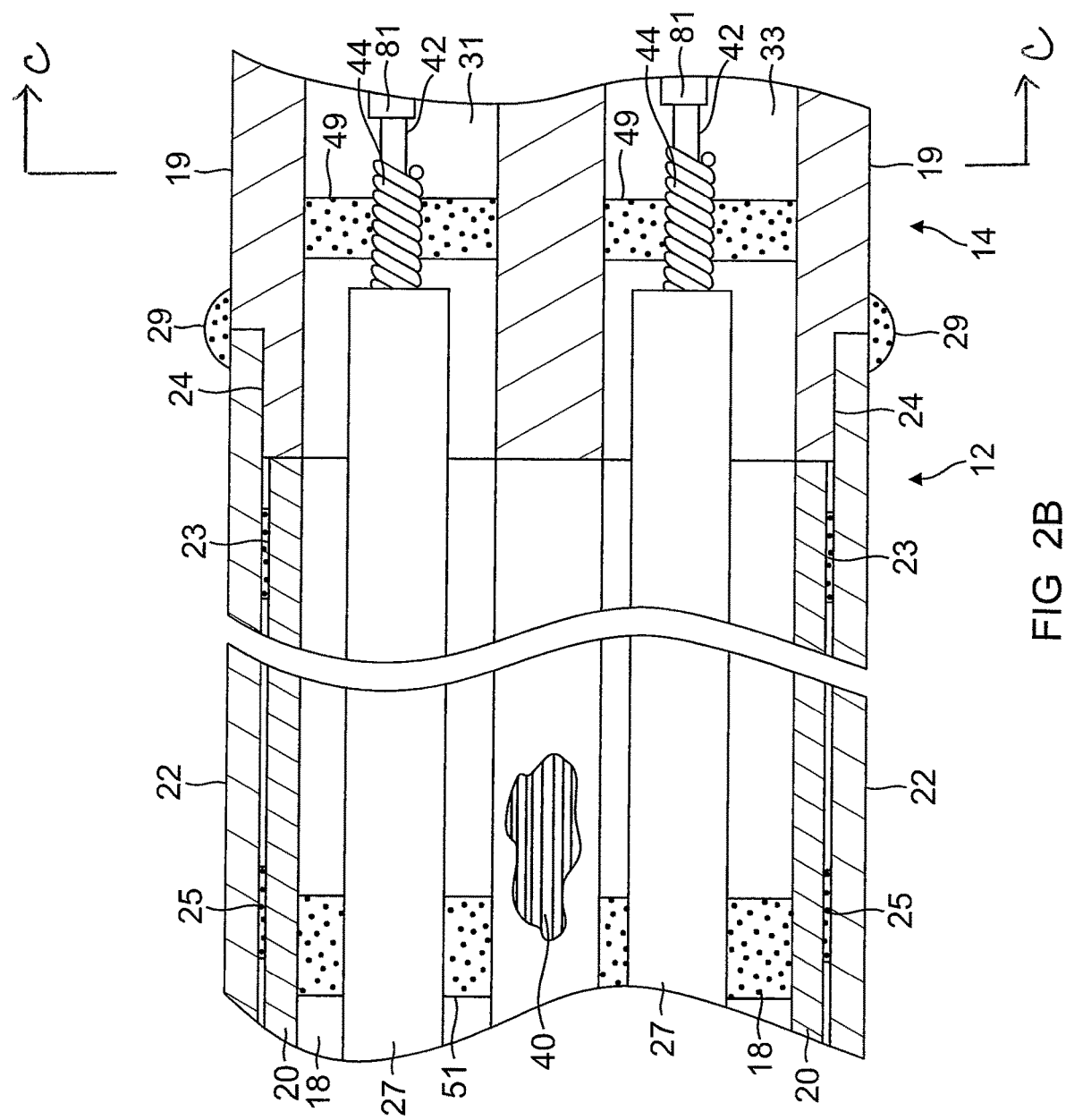
FIG. 2B is a side cross-sectional view of the junction of FIG. 2A, taken along a second diameter generally perpendicular to the first diameter.

With reference to FIGS. 2A and 2B, the catheter body 12 comprises a single, central or axial lumen 18. The catheter body 12 is flexible, i.e., bendable, but substantially non-compressible along its length. The catheter body 12 may be of any suitable construction and made of any suitable material. In one embodiment, the catheter body 12 comprises an outer wall 22 made of a polyurethane or nylon. The outer wall 22 comprises an imbedded braided mesh of stainless steel or the like to increase torsional stiffness of the catheter body 12 so that, when the control handle 16 is rotated, the tip section of the catheter 10 will rotate in a corresponding manner.

The outer diameter of the catheter body 12 is not critical, but is preferably no more than about 8 French. Likewise the thickness of the outer wall 22 is not critical. The inner surface of the outer wall 22 is lined with a stiffening tube 20, which can be made of any suitable material, preferably polyimide. The stiffening tube 20 is held in place relative to the outer wall 22 at the proximal end of the catheter body 12. A first glue joint 23 is made between the distal ends of the stiffening tube 20 and the outer wall 22 by a fast drying glue, e.g. Super Glue®. Thereafter, a second glue joint 25 is formed between the proximal ends of the stiffening tube 20 and outer wall 22 using a slower drying but stronger glue, e.g., polyurethane.

The stiffening tube 20, along with the braided outer wall 22, provides improved torsional stability while at the same time minimizing the wall thickness of the catheter, thus maximizing the diameter of the single lumen. The outer diameter of the stiffening tube 20 is about the same as or slightly smaller than the inner diameter of the outer wall 22. Polyimide tubing is suitable because it may be very thin walled while still providing very good stiffness. This maximizes the diameter of the central lumen 18 without sacrificing strength and stiffness. Polyimide material is typically not used for stiffening tubes because of its tendency to kink when bent. However, it has been found that, in combination with an outer wall 22 of polyurethane, nylon or other similar material, particularly having a stainless steel braided mesh, the tendency for the polyimide stiffening tube 20 to kink when bent is essentially eliminated with respect to the applications for which the catheter is used.

In one embodiment, the outer wall 22 has an outer diameter of about 0.092 inch and an inner diameter of about 0.063 inch and the polyimide stiffening tube 20 has an outer diameter of about 0.0615 inch and an inner diameter of about 0.052 inch.

Figure 2C:
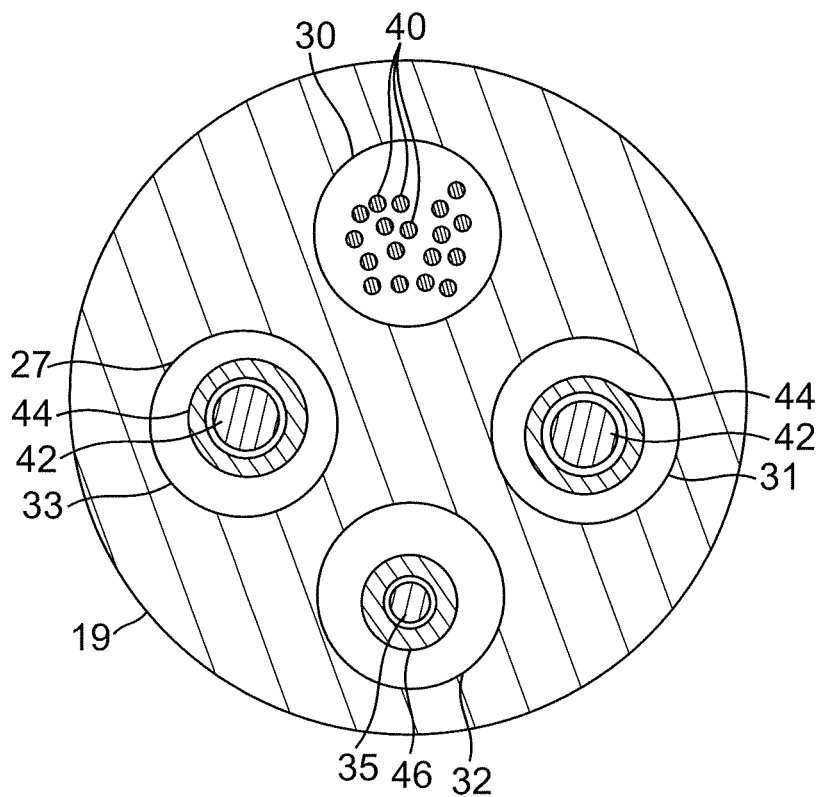
FIG. 2C is an end cross-sectional view of the intermediate section of FIGS. 2A and 2B, taken along line C-C.

As shown in FIGS. 2A, 2B and 2C, the intermediate section 14 comprises a shorter section of tubing 19 with multiple lumens, for example, first, second, third and fourth lumens 30, 31, 32 and 33. The tubing 19 is made of a suitable non-toxic material which is preferably more flexible than the catheter body 12. A suitable material for the tubing 19 is braided polyurethane, i.e., polyurethane with an embedded mesh of braided stainless steel or the like. The outer diameter of the intermediate section 14, like that of the catheter body 12, is preferably no greater than about 8 French. The size of the lumens is not critical. In one embodiment, the intermediate section has an outer diameter of about 7 French (0.092 inch) and the lumens are generally about the same size, having a diameter of about 0.022 inch, or selected lumens can have a slightly larger diameter of about 0.036 inch.

A means for attaching the catheter body 12 to the intermediate section 14 is illustrated in FIGS. 2A and 2B. The proximal end of the intermediate section 14 comprises an inner counter bore 24 that receives the outer surface of the polyimide stiffener 20. The intermediate section 14 and catheter body 12 are attached by glue 29 or the like.

As shown in FIGS. 2A and 2B, extending through the single lumen 18 of the catheter body 12 are various components, for example, lead wires and multiple puller wires, and any other wires or cables. Longitudinal movement of the puller wires relative to the catheter body 12 enables user control of various parts of the catheter via the control handle. In one embodiment, there are a pair of deflection puller wires 42 for deflecting the intermediate section 14 and a contraction puller wire 35 for adjusting the distal assembly 17 of the tip section 15.

A single lumen catheter body 12 may be preferred over a multi-lumen body because the single lumen 18 body can permit better tip control when rotating the catheter 10. The single lumen 18 permits the components passing therethrough to float freely within the catheter body. If such components were restricted within multiple lumens, they can build up energy when the handle 16 is rotated, resulting in the catheter body 12 having a tendency to rotate back if, for example, the handle is released, or if bent around a curve, to flip over, either for which are undesirable performance characteristics.

One deflection puller wire 42 extends through the central lumen 18 of the catheter body 12 and into the second lumen 31 of the intermediate section 14. Another deflection puller wire 42 extends through the central lumen 18 and into the fourth lumen 33 of the intermediate section 14. In that regard, the lumens 31, 33 should be off-axis and diametrically opposed to each other for bi-directional deflection in a plane. The distal ends of the deflection puller wires 42 are anchored to the wall of the tubing 19 near the distal end of the intermediate section 14 by means of T-anchors (not shown) as understood by one of ordinary skill in the art. In the intermediate section 14, each deflection puller wires 42 extends through a plastic, e.g. Teflon®, sheath 81, which prevents the deflection puller wires 42 from cutting into the wall of the tubing 19 of the intermediate section 14 when the intermediate section 14 is deflected.

As shown in FIG. 2B, compression coils 44 in surrounding relation to the deflection puller wires 42 extend from the proximal end of the catheter body 12 to the proximal end of the intermediate section 14. The compression coils 44 are made of any suitable metal, e.g., stainless steel. The compression coils 44 are tightly wound on itself to provide flexibility, i.e., bending, but to resist compression. The inner diameter of the compression coils 44 is preferably slightly larger than the diameter of the puller wires 42. For example, when a puller wire 42 has a diameter of about 0.007 inches, the compression coil 44 preferably has an inner diameter of about 0.008 inches. The Teflon® coating on the puller wire 42 allows them to slide freely within the compression coils 44. The outer surface of the compression coils 44 is covered by a flexible, non-conductive sheath 27 to prevent contact between the compression coils 44 and other components, such as lead wires and cables, etc. In one embodiment, a non-conductive sheath is made of polyimide tubing.

The compression coils 44 are anchored at their proximal ends to the proximal end of the stiffening tube 20 in the catheter body 12 by glue joint 50 (FIG. 2B) and at its distal end near the proximal end of the intermediate section 14 in the second lumen 31 and fourth lumen 33 by glue joints 49 (FIG. 2B).

Figure 3A:
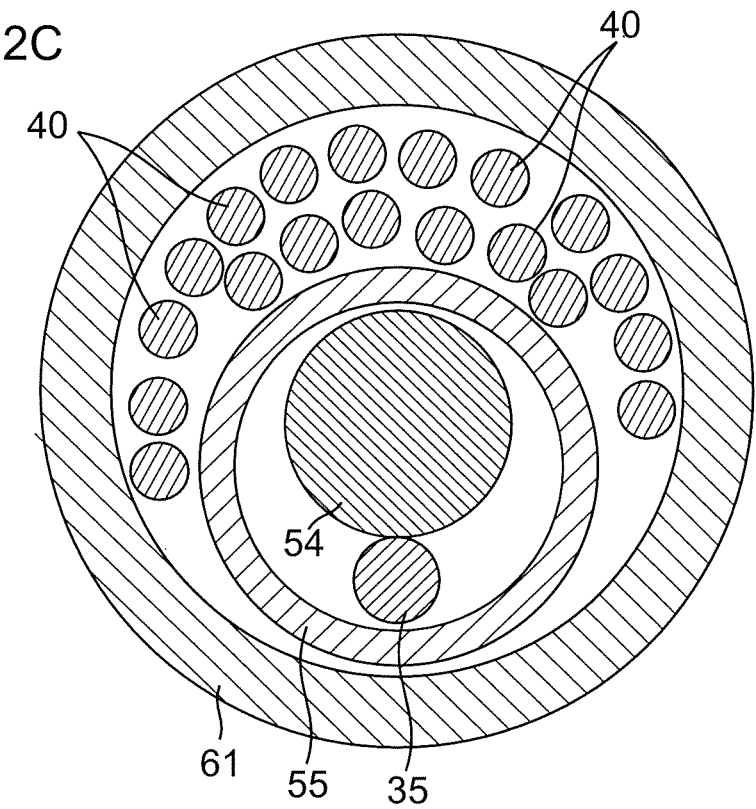
FIG. 3A is an end cross-sectional view of the distal assembly of FIG. 3, taken along line A-A.

With reference to FIG. 1, at the distal end of the intermediate section 14 is the distal assembly 17 for mapping and/or ablation. As illustrated in FIGS. 3 and 3A, the distal assembly 17 comprises a generally straight proximal region 38 and a generally circular main region 39. The proximal region 38 is mounted on the intermediate section 14 and the generally circular main region carries a plurality of electrodes for mapping and/or ablation. In the illustrated embodiment, the distal assembly includes a tubing 61. A shape memory member 54 and a third puller member or contraction wire 35 extend through a nonconductive protective tubing 55, which in turn extends through the lumen of the tubing 61 along with lead wires 40 for electrodes carried on the distal assembly.

In the disclosed embodiment, the contraction puller wire 35 is provided to contract the generally circular main region 39 to thereby change or reduce its diameter, for example, when mapping or ablating circular or tubular regions of the heart. The contraction wire 35 has a proximal end anchored in the control handle 16 as described further below. As illustrated in FIG. 2A, the contraction wire 35 extends through the central lumen 18 of the catheter body 12, through the third lumen 32 of the intermediate section 14 and into the distal assembly 17.

A third compression coil 46 is situated within the catheter body 12 and intermediate section shaft 14 in surrounding relation to the contraction wire 35 (FIG. 2A). The third compression coil 46 extends from the proximal end of the catheter body 12 and to near the distal end of the third lumen 32 of the intermediate section 14. The third compression coil 46 is made of any suitable metal, such as stainless steel, and is tightly wound on itself to provide flexibility, i.e., bending, but to resist compression. The inner diameter of the third compression coil 46 is preferably slightly larger than the diameter of the contraction wire 35. The outer surface of the compression coil 46 is covered by a flexible, non-conductive sheath 68, e.g., made of polyimide tubing. The third compression coil 46 preferably is formed of a wire having a square or rectangular cross-sectional area, which makes it less compressible than a compression coil formed from a wire having a circular cross-sectional area. As a result, the third compression coil 46 keeps the catheter body 12, and particularly the intermediate section 14, from deflecting when the contraction wire 35 is manipulated to contract the distal assembly 17 as it absorbs more of the compression.

The third compression coil 46 is anchored at its proximal end to the stiffening tube 20 of the catheter body 12 by the proximal glue joint 50 and to the intermediate section 14 by distal glue joint 73.

It is understood that glue joints throughout the catheter 10 may comprise polyurethane glue or the like. The glue may be applied by means of a syringe or the like through a hole made in the tubing walls. Such a hole may be formed, for example, by a needle or the like that punctures the tubing walls where the needle is heated sufficiently to form a permanent hole. The glue is then introduced through the hole to wick around the component(s) within the tubing to form a glue joint about the entire circumference of the component(s).

The lead wires 40 attached to the ring electrodes on the distal assembly 17 extend through the first lumen 30 of the intermediate section 14 (FIG. 2A), through the central lumen 18 of the catheter body 12, through the control handle 16, and terminate at their proximal end in a connector (not shown) which is connected to an appropriate monitor or other device for receiving and displaying the information received from the ring electrodes. The portion of the lead wires 40 extending through the central lumen 18 of the catheter body 12, control handle 16 and proximal end of the intermediate section 14 is enclosed within a protective sheath 62, which can be made of any suitable material, preferably polyimide.

An electromagnetic position sensor (not shown) is mounted in or near the distal assembly 17. A sensor cable 36 extends from the sensor into the lumen 30 of the intermediate section (along with the electrode lead wires 40), into the central lumen 18 of the catheter body 12 and into the control handle where it terminates in a suitable connector (not shown).

With reference to FIG. 1, the control handle 16 comprises a generally elongated handle housing, which can be made of any suitable rigid material, such as plastic configured through a suitable molding process. In the illustrated embodiment, the housing includes two opposing halves 16a and 16b that generally mirror each other and are joined by glue, sonic welding or other suitable means along a longitudinal peripheral seam 28 around the housing.

The control handle 16 houses components of a deflection control assembly 13 that includes a deflection dial 50 for bi-directional deflection of the intermediate section 14 via the first and second puller wires 42. As illustrated in FIGS. 4 and 5A-5C, by rocking the deflection dial (represented by arrow 50) in one direction, the puller wire 42 in that direction is drawn proximally to deflect the intermediate section 14 in that direction.

Each puller wire 42 is made of any suitable metal, such as stainless steel or Nitinol. Preferably each puller wire has a low friction coating, such as a coating of Teflon® or the like. Each puller wire has a diameter preferably ranging from about 0.006 inch to about 0.012 inch. Preferably both of the puller wires have the same diameter. Flat puller wires may be used in place of round puller wires. Their cross sectional dimensions should be such that they provide comparable tensile strengths as round puller wires. Alternatively, tensile fibers can be used in whole or in part. They may be of a high modulus fiber material, preferably having an ultimate tensile strength substantially in the range of 412-463 ksi (2480-3200 Mpa) such as High Molecular Density Polyethylene (e.g., Spectra™ or Dyneema™), a spun para-aramid fiber polymer (e.g., Kevlar™) or a melt spun liquid crystal polymer fiber rope (e.g., Vectran™), or a high strength ceramic fiber (e.g., Nextel™). The term fiber is used herein interchangeably with the term fibers in that the tensile fiber may be of a woven or braided construction. In any case, these materials tend to be flexible, providing suitable durability when used in wrapped engagement with the pulleys and the like for greater throw in deflecting the catheter tip. Further, they are substantially non-stretching, which increases the responsiveness to the manipulation of the control handle, and nonmagnetic so that they generally appear transparent to an MRI. The low density of the material causes it to be generally transparent to an x-ray machine. The materials can also be nonconductive to avoid shorting. Vectran™, for example, has high strength, high abrasion resistance, is an electrical insulator, nonmagnetic, is polymeric, and has low elongation under sustained loading conditions. In the illustrated embodiment of FIG. 4, each puller member 42 includes a distal puller wire portion 42D and a proximal tensile fiber portion 42P joined by a connector 81.

Figure 6:
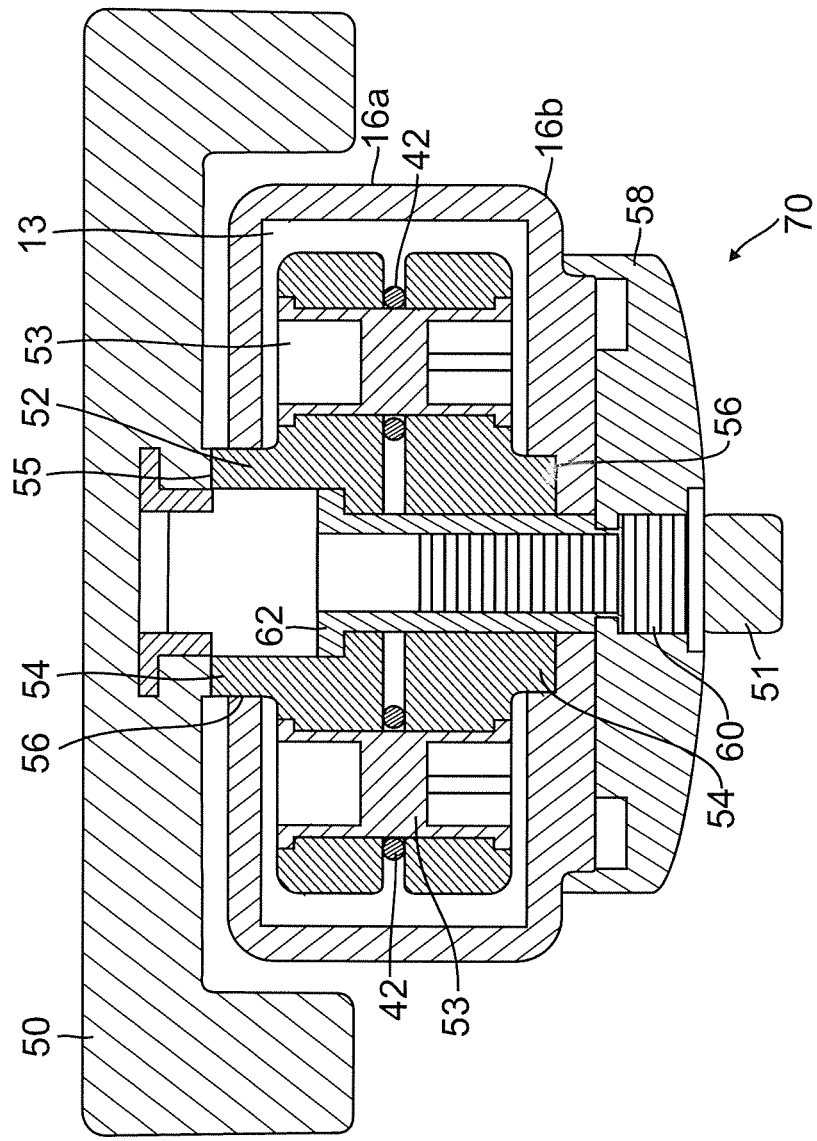
FIG. 6 is an end cross-sectional view of an embodiment of a deflection assembly within a control handle.

The construction and assembly of the deflection control assembly 13 including the deflection knob 50 and a tension adjustment knob 51 on the control handle 16 are described as follows. A rocker arm 52 of the assembly 13 is situated between the two halves 16A and 16B of the control handle 16. With further reference to FIG. 6, each of top and bottom radial bearing sleeves formed as annular projections 54 of the rocker arm 52 extends into a respective opening 56 formed in each of the housing half 16A, 16B.

The deflection knob 50 and the rocker arm 52 are rotationally coupled to each other by interlocking features at their mating surfaces 55. Opposing the deflection knob 50 is the tension adjustment knob 51 which is coupled to and indirectly engaged with the rocker arm 52 by various mechanisms and parts. The knob 51 allows an operator to adjust the ease with which the deflection arm 75 can be rotated. The illustrated embodiment of the tension adjustment knob 51 is part of a tension adjustment assembly 70 that also includes a cap 58 rotationally coupled to the knob 52, a friction screw 60 that is rotationally coupled to the cap 58, and a friction nut 62 that is in engagement with the friction screw 60. A user rotates the knob 51 to adjust the tightness or tension of the rotational movement of deflection knob 50 by effectively applying or releasing a compression load on the components of the assemblies to increase or decrease frictional torque between contacting surfaces of the components. A suitable deflection assembly is described in U.S. Pat. No. 7,377,906, the entire disclosure of which is hereby incorporated by reference.

For manipulating the distal assembly 17 by means of a third puller wire, e.g., the contraction wire 35, a proximal end of the contraction wire is anchored in the control handle 16 for actuation by a spool assembly 80 housed in the control handle 16. In the disclosed embodiment, the spool assembly 80 is distal of the deflection assembly 13 in the control handle.

Figure 7:
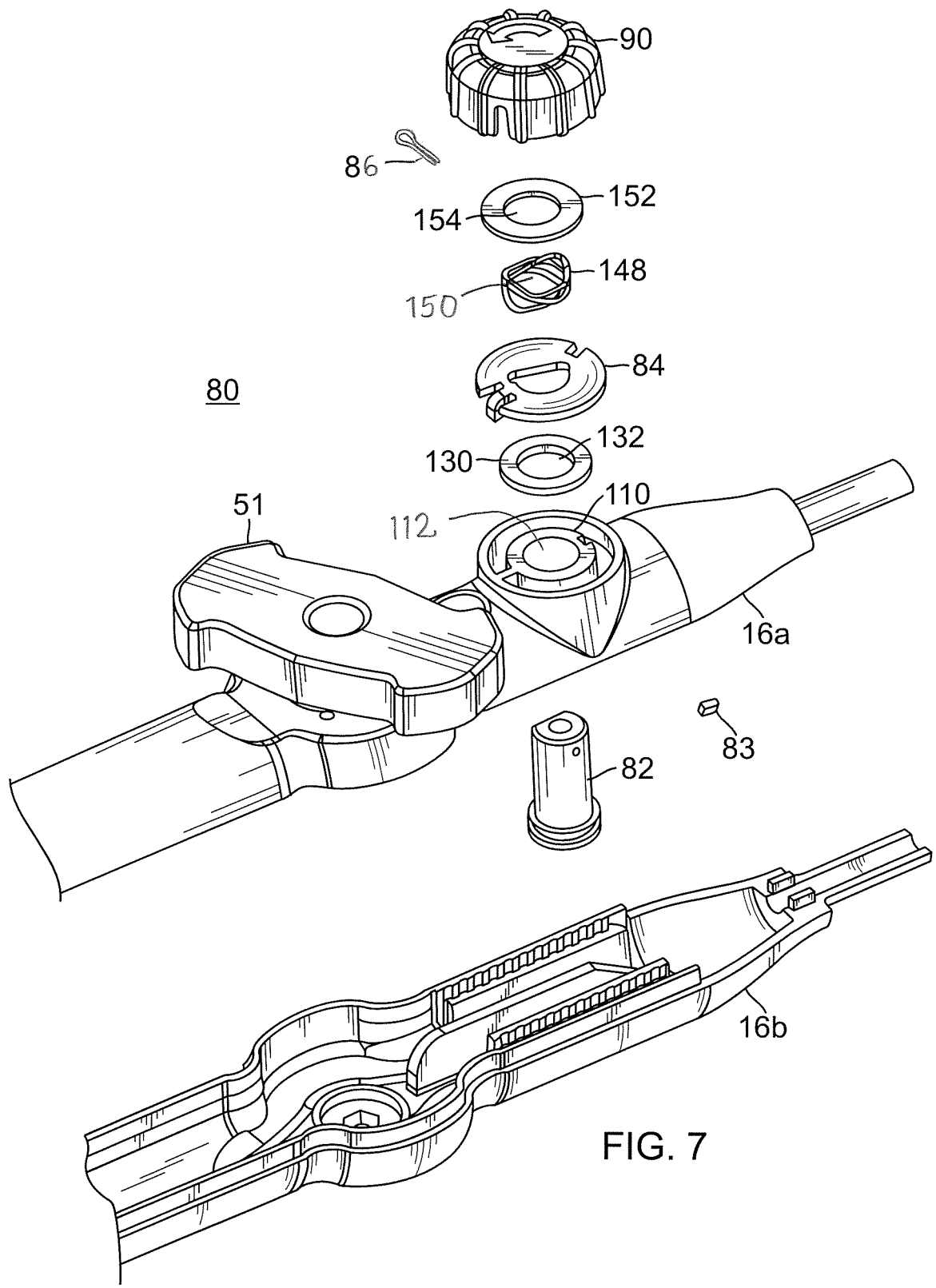
FIG. 7 is an exploded perspective view of an embodiment of an additional puller member actuator assembly.
Figure 8:
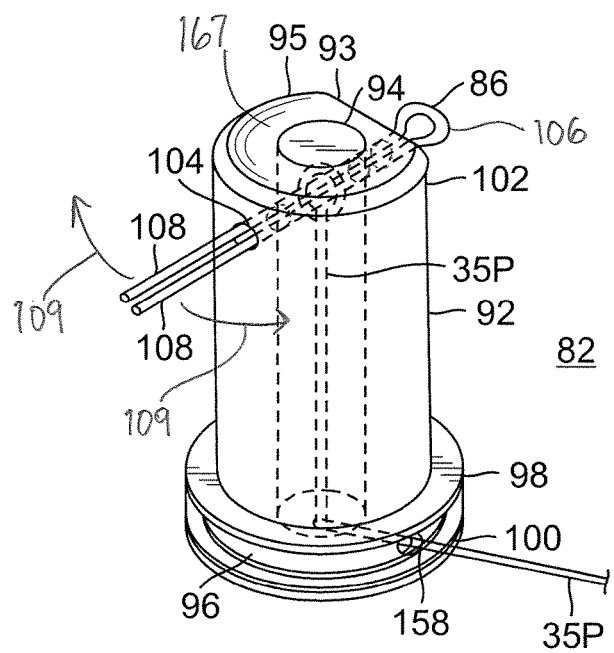
FIG. 8 is a perspective view of the spool shaft of FIG. 7.
Figure 9:
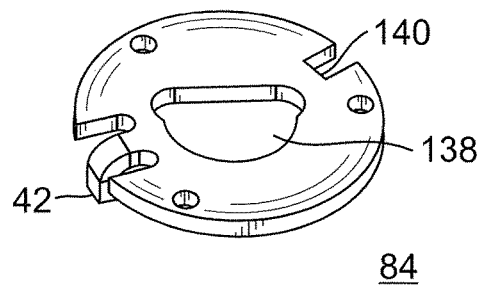
FIG. 9 is a perspective view of the detent tab washer of FIG. 7.
Figure 11A:
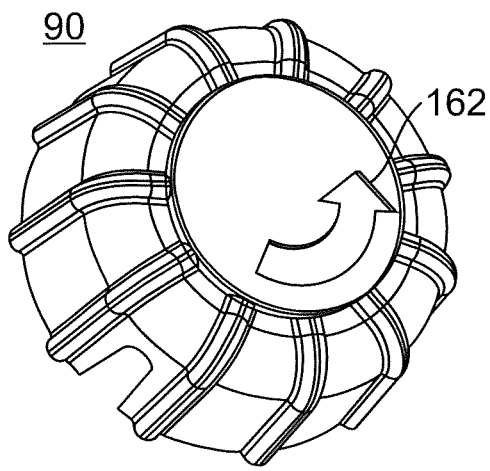
FIG. 11A is a perspective top view of the dial of FIG. 7.
Figure 11B:
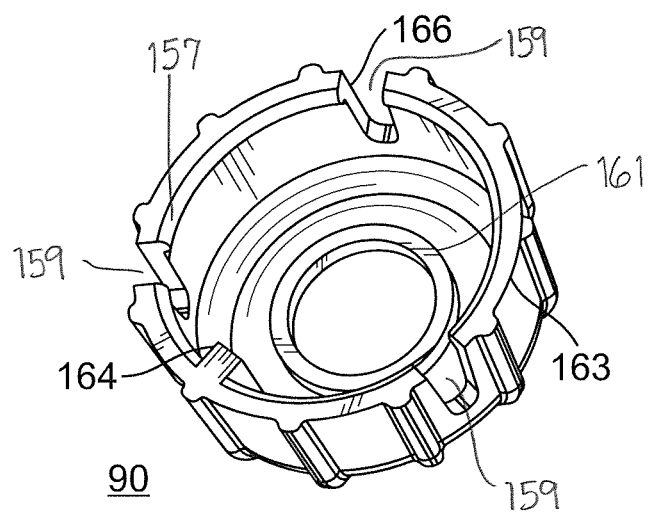
FIG. 11B is a perspective bottom view of the dial of FIG. 7.

In the illustrated embodiment of FIG. 7, the spool assembly 80 includes a take-up spool 82 (FIG. 8), a contraction wire anchor pin 86 (FIG. 8), a detent tab washer 84 (FIG. 9) and a user interface dial 90 (FIGS. 11A and 11B). Best shown in FIG. 8, the spool 82 has an elongated shaft body 92 with a longitudinal bore 94 extending therethrough. The shaft body 92 has an outer cross-sectional shape that is noncircular or radially asymmetrical so that the body can receive and transfer rotational torque. In the disclosed embodiment, the cross-sectional shape is of a D shape to form an elongated planar outer surface 93. One end of the shaft body 92 is formed with a take-up drum 96 between an inner rim 98 and an outer rim 100, where at least the inner rim 98 has a diameter larger than a diameter of the shaft body 92. At an opposing end 102 of the shaft body, a transverse through-hole 104 is formed at the end 102 to receive the contraction wire anchor pin 86, e.g., a Cotter pin with a head 106 and two parallel legs 108.

The spool assembly 80 also includes a plurality of washers for locking and/or inducing friction to render the dial 90 self-holding so that the dial 90 maintains its position when released by the user during hands-free operation.

Figure 10:
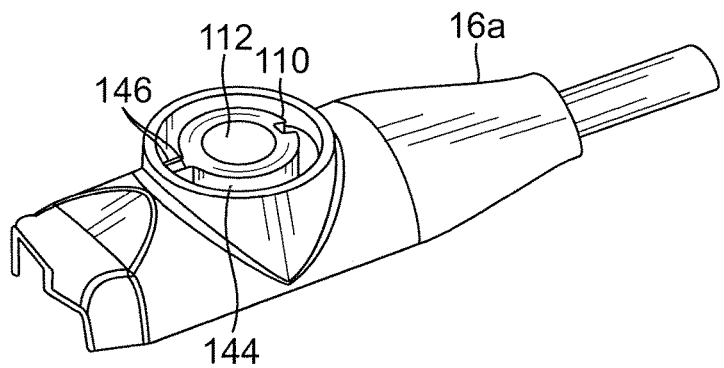
FIG. 10 is a perspective view of the control handle housing half of FIG. 7.

A radial bearing sleeve 110 (FIG. 10) is formed in control handle housing half 16a to provide a through-hole 112. The shaft body 92 of the spool 82 is received in the through-hole 112 which is sized smaller than the inner rim 98 so that the drum remains in the interior of the housing half 16a. The majority of the shaft body 92 with the end 102 extends through the sleeve 110 to outside of the housing half 16a. For ease of reference only, the relative position of various components is described herein as being above or below each other, although it is understood that the control handle and its interior components can be assembled and used in any orientation.

Mounted on the shaft body 82 immediately above the sleeve 110 is a base washer 130 (FIG. 7) with a circular center bore 132. As such, the base washer is rotationally independent of (or not strictly rotationally coupled to, used interchangeably herein) the spool 82.

Immediately above the base washer 130 is the detent tab washer 84. Best seen in FIG. 9, the detent tab washer has a noncircular central bore 138 that corresponds in size and shape to the outer cross-section of the shaft body 92 of the spool 82 so that it is rotationally coupled to the spool. On a peripheral edge of the detent tab washer is a recessed formation or notch 140 for rotationally coupling with the dial 90, as explained further below. Also on the peripheral edge is a tab 142 extending transversely, e.g., downwardly. The tab 142 sits in a recessed channel 144 (FIG. 10) provided on the outer surface of the control handle housing half 16a surrounding the radial bearing sleeve 110. The circular channel 144 extends a predetermined range of angle around the sleeve between two ends or stops 146 which limit the range the amount of rotational travel of the detent tab washer 84 and thus the range a user can rotate the dial 90. Without such limitation, the contraction wire can be subject to damage, for example, when drawn excessively to the point of breakage. In the disclosed embodiment, the channel 144 extends about 350 degrees around the sleeve 110.

Mounted on the shaft body 92 and immediately above the detent tab washer 84 is a washer 148 (FIG. 7) adapted for compression loading. The washer may be a wave washer or clover washer or a curved disk Belleville type spring washer. The washer 148 has a circular center bore 150 so that it is not strictly rotationally coupled to the spool 82.

Further mounted on the shaft body 92 immediately above the compression loading washers 148 is a washer 152 with a circular center bore 154. The washer 152 is also rotationally independent of the spool 82.

Similar to the deflection puller members 42, the contraction wire 35 may have a distal wire portion 35D and a proximal tensile fiber portion 35P (FIG. 4). The tensile fiber portion 35P is inserted through a transverse hole 158 (FIG. 8) formed in the drum 96 that communicates with the center longitudinal through-bore 94 of the shaft body 92 of the spool 82. The tensile fiber portion 35P is fed up the bore 94 toward the end 102 to reach the anchor pin 86 and anchored to the legs 108 inserted through the holes 104. The anchor pin 86 is rotated about its longitudinal axis to take up slack and apply a suitable tension to the contraction wire 35. The legs 108 are then separated and wrapped in opposite directions (arrows 109) about the shaft body 92 to lock the pin 86 in place.

Immediately above the locking washer 152 is the dial 90. As shown in FIG. 11A, the dial has a cap body with an outer top surface of the dial 90 has a visual indicia 162, e.g., an arrow indicating a direction of rotation for drawing the contraction wire. At an underside of the dial, a peripheral wall 163 is formed with a rib 164 to correspond and engage with the notch 140 formed in the detent tab washer 84 for rotational coupling between the dial and the detent tab washer. As such, the dial 90 is rotationally coupled to the spool 82 by means of the detent tab washer 84. As a user rotates the dial 90, the dial effectively rotates the spool 82 whose drum end 96 draws the tensile fiber portion 35b of the contraction wire onto the drum 96. The tab 142 of the detent tab washer 84 riding in the channel 144 of the radial bearing sleeve 110 guides the rotation of the dial 90. The stops 146 in the channel limit the rotation of the dial 90. Thus, the stops 146 effectively limits the travel of the contraction wire 35 by which a user can actuate by means of the dial so as to prevent the user from damaging the contraction wire, including over-rotating and breakage.

The dial 90 is snap fitted onto the detent tab washer 94. As shown in FIG. 11B, a circumferential lip 157 is formed around a bottom edge of the peripheral wall 163 of the dial 90. The lip 157 rides over and catches the peripheral edge of the detent tab washer 94 as the dial 90 is pressed onto the shaft body 92. A plurality of slots 159 formed in and evenly spaced around the peripheral wall of the dial 90 allow the cap body to elastically expand outwardly and snap onto the detent tab washer. A radial ridge 161 formed on the underside of the cap body contacts top surface 167 of the shaft body 92.

Figure 12:
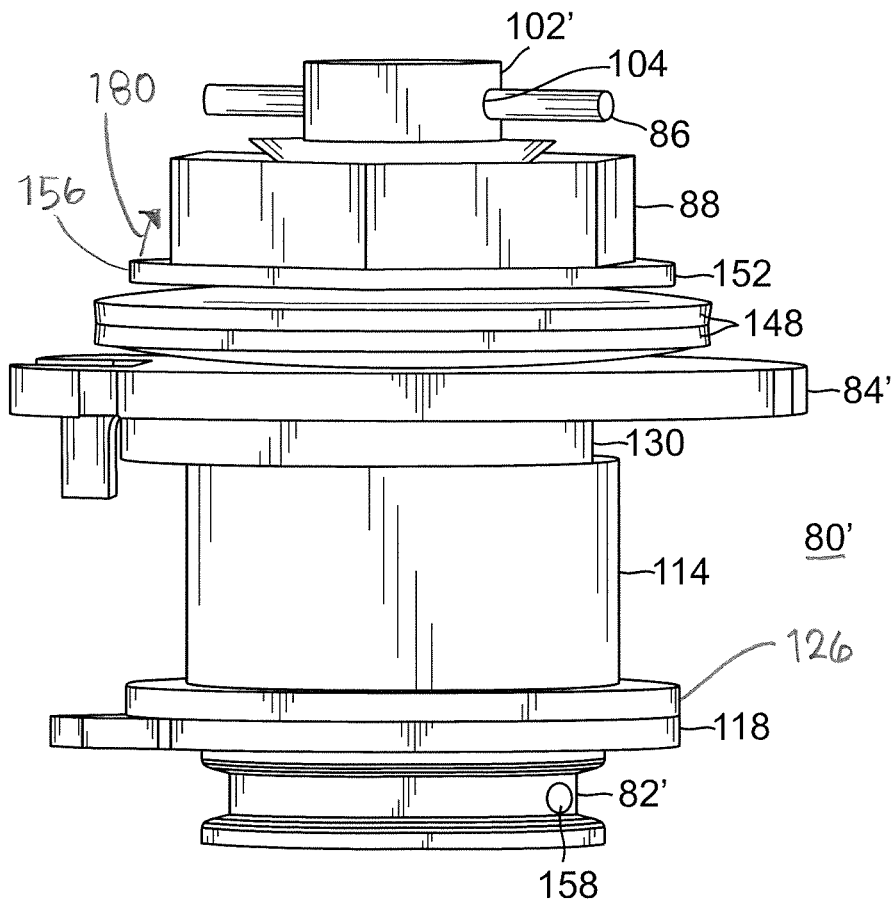
FIG. 12 is a side view of an alternate embodiment of an additional puller member actuator assembly.
Figure 13:
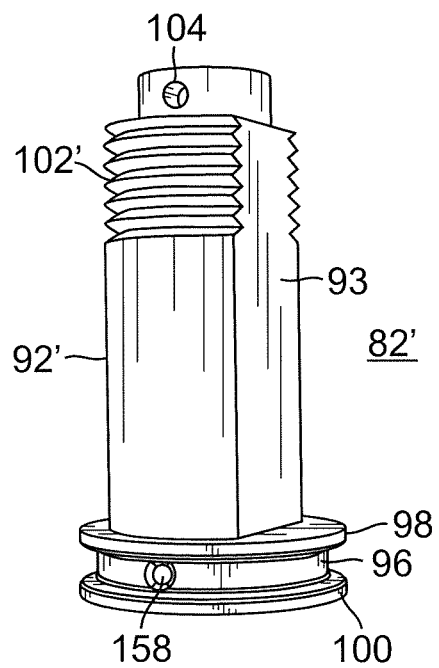
FIG. 13 is a perspective view of the spool shaft of FIG. 12.
Figure 18:
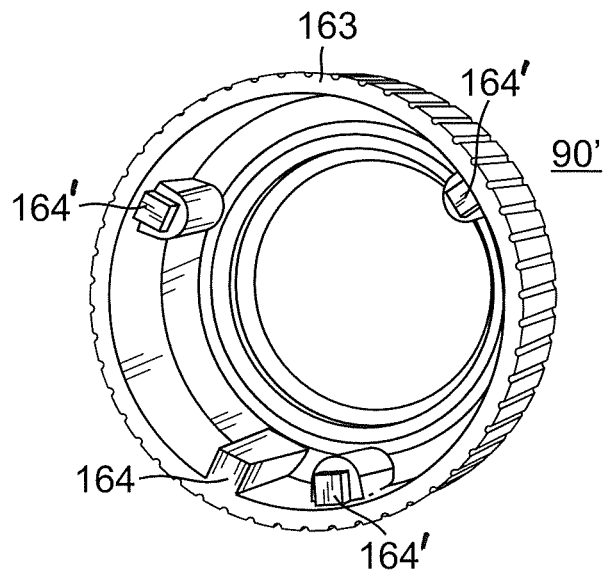
FIG. 18 is a perspective bottom view of the dial of FIG. 12.

In an alternate embodiment as illustrated in FIG. 12, a spool assembly 80' includes a take-up spool 82' (FIG. 13), the contraction wire anchor pin 86, a detent tab washer 84' (FIG. 16), a fastener 88, and a user interface dial 90' (FIG. 18). The spool 82' has an elongated shaft body 92' with a longitudinal bore 94 (see, e.g., FIG. 8). The shaft body 92' has an cross-sectional shape that is noncircular or radially asymmetrical so that the body can receive and transfer rotational torque. In the disclosed embodiment, the cross-sectional shape is of a D shape so that the shaft body has an elongated planar outer surface 93. One end of the shaft body 92 is formed with a take-up drum 96 between an inner rim 98 and an outer rim 100, where at least the inner rim 98 has a diameter larger than a diameter of the shaft body 92. An opposing end 102' of the shaft body 92 is threaded for receiving the fastener 88, e.g., a hex jam nut. A transverse through-hole 104 is formed at the threaded end 102 to receive the contraction wire anchor pin 86, e.g., a Cotter pin (see FIG. 8).

The spool assembly 80' also includes a plurality and combination of washers for locking and/or inducing friction to render the dial 90' self-holding so that the dial 90' maintains its position when released by the user during hands-free operation.

Figure 19:
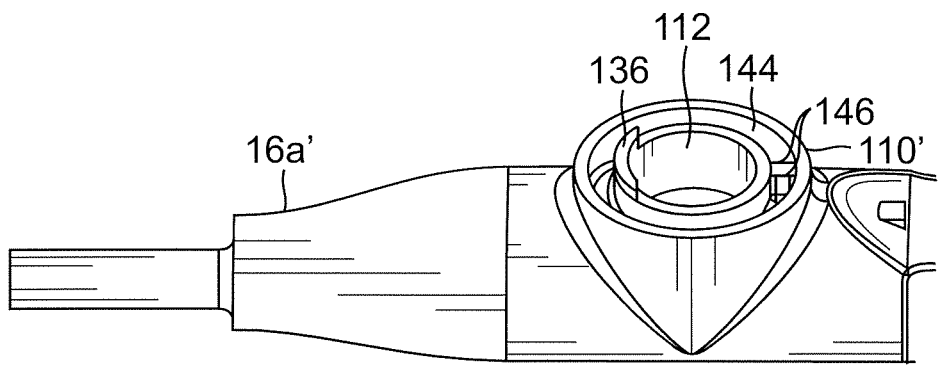
FIG. 19 is a perspective view of an exterior of the control handle housing half of FIG. 12.

A radial bearing sleeve 110' (FIG. 19) is formed in control handle housing half 16a' to provide a through-hole 112. The shaft body 92' of the spool 82' is received in the through-hole 112 which is sized smaller than the inner rim 98. The shaft body 92 is lined with a bushing 114 (FIG. 12) which prevents plastic creep during long term compression loading where the control handle is constructed of nonglass or noncarbon fiber reinforced thermoplastics. The majority of the shaft body 92' with the threaded end 102' extends through the sleeve 110' to outside of the housing half.

Figure 14:
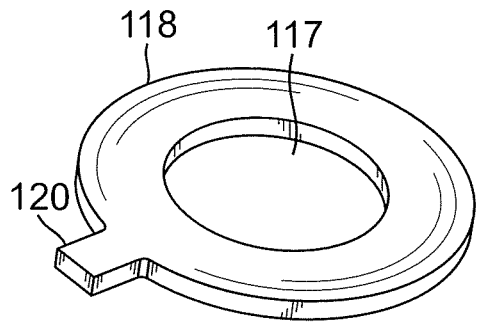
FIG. 14 is a perspective view of the tabbed washer of FIG. 12.

In the disclosed embodiment of FIG. 12, a washer 118 is mounted on the shaft body 92 of the spool 82 immediately above the inner rim 98 and sits inside the control handle housing half. The washer 118 (FIG. 14) has a circular center bore 117 and a tab 120 extending from its peripheral edge which is received in a corresponding slot 122 extending from a circular recess 124 (FIG. 20) formed in an inner surface of the control handle housing half 16a. The tab 120 received in the slot 122 locks the washer 118 against rotation relative to the spool 82' and the control handle housing half 16a.

Figure 15:
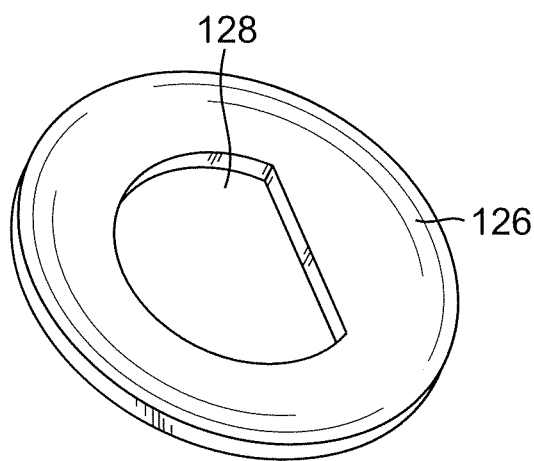
FIG. 15 is the perspective view of a friction washer of FIG. 12.
Figure 20:
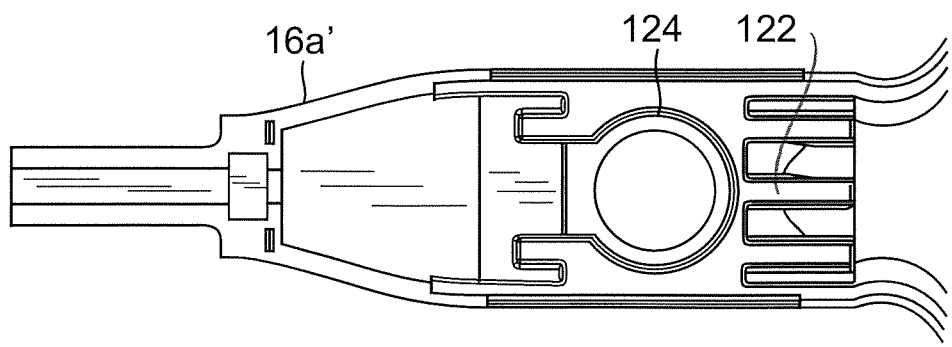
FIG. 20 is a perspective view of an interior of the control handle housing half of FIG. 12.

Immediately above the tabbed washer 118 on the shaft body 92 is a rotational washer 126 (FIG. 15) having a central bore 128 of a corresponding size and shape to the size and shape of the shaft body 92, e.g., a D-shape, so that it is rotationally coupled to the spool 82. The rotational washer 126 also sits inside of the control handle housing half 16a, within the circular recess 124 (FIG. 20). The rotational washer 126 and the non-rotating tabbed washer 118 are in contact with each other on their adjacent surfaces so as to generate friction to help render the dial 90 self-locking when the spool 82 is rotated relative to the control handle housing half 16a with the assembly 80' being under compression.

Immediately above the rotational washer 126 on the shaft body 92 is the bushing 114 (FIG. 12) which circumferentially lines the through-bore 112 of the sleeve 110. The bushing has a predetermined length such that its outer end sits flush with the outer surface of the sleeve 110' of the control handle housing half 16a.

Figure 17:
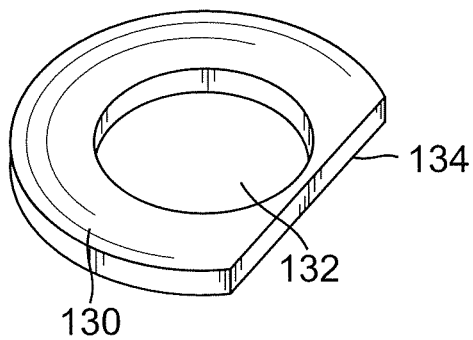
FIG. 17 is a perspective view of an engagement washer of FIG. 12.

Immediately above the bushing 114 is a base washer 130 (FIG. 17) with a circular center bore 132. A peripheral edge is provided with an engagement formation 134, e.g., a straight edge portion, which engages and abuts a ridge 136 (FIG. 19) formed on the outer surface of the sleeve 110' so as to lock the base washer 130 against rotation relative to the spool 82' and the control handle housing half 16*a* for purpose of generating friction.

Figure 16:
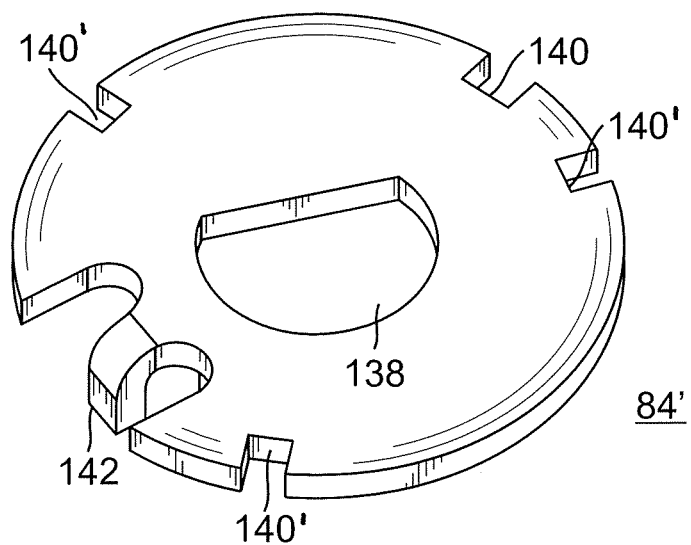
FIG. 16 is a perspective view of the detent tab washer of FIG. 12.

Immediately above the base washer 130 is detent tab washer 84' (FIG. 16). The detent tab washer also has a noncircular central bore 138 that corresponds in size and shape cross-section of the shaft body 92 of the spool 82 so that it is rotationally coupled to the spool. On a peripheral edge of the detent tab washer are a plurality of recessed formation or notches 140. In the illustrated embodiment, there are four notches 140 distributed around the peripheral edge for rotational coupling with the dial 90'. Also on the peripheral edge is a tab 142 extending transversely, e.g., downwardly. The tab 142 sits in a recessed channel 144 provided on the outer surface of the control handle housing half 16*a*' surrounding the radial bearing sleeve 110. The circular channel 144 extends a predetermined range of angle around the sleeve between two ends or stops 146 which limit the range the amount of rotational travel of the detent tab washer 84 and thus the range a user can rotate the dial 90. Without such limitation, the contraction wire can be subject to damage, for example, when drawn excessively to the point of breakage. In the disclosed embodiment, the channel 144 of FIG. 19 also extends about 350 degrees around the sleeve 110.

Mounted on the shaft body 92' and immediately above the detent tab washer 84' is a pair of washers 148 adapted for compression load, e.g., slotted Belleville washers. The washers have a circular center bore so that they are rotationally independent from the shaft body 92 of the spool 82.

Further mounted on the shaft body 92 immediately above the pair of compression washers 148 is a washer 152 with a circular center bore 154. The washer 152 is also rotationally independent of the spool 82.

Immediately above the washer 152 is the fastener 88, e.g., the hex jam nut, that is screwed on the threaded end 102 of the shaft body 92. The fastener 88 is tightened on the shaft body 92 to generate a compression load on the pair of washers 148 so as to provide friction with the various contacting surfaces of the washers of the assembly 80. An edge portion 156 of the washer 152 can be turned up around (arrow 180) an edge of the hex jam nut to hold the nut in place and prevent it from loosening. An alternate method to lock the nut in place is to use a retaining compound such as LOCTITE 272 permanent thread locker adhesive.

The tensile fiber portion 35P of the contraction wire 35 is inserted through a transverse hole 158 formed in the drum 96 that communicates with the center longitudinal through-bore 94 of the shaft body 92' of the spool 82'. The tensile fiber portion 35P is fed up the bore toward the end 102 to reach the anchor pin 86 and anchored in a similar fashion as described above Above the anchor pin 86 is the dial 90'. In the disclosed embodiment, the cap body is ultrasonically welded or adhesive bonded onto the detent tab washer 94'. As shown in FIG. 18, a peripheral wall 163 is formed with a plurality of ribs 164 to correspond and engage with the notches 140 formed in the detent tab washer 84 for rotational coupling between the dial and the detent tab washer. A larger/wider rib 164 corresponds in size and shape to the larger/wider notch 140. Smaller/narrower ribs 164' correspond in size and shape to the smaller/narrower notches 140' which are ultrasonically welded or adhesive bonded to each other. As such, the dial 90 is rotationally coupled to the spool 82 by means of the detent tab washer 84. As a user rotates the dial 90, the dial rotates the spool 82 whose drum end 96 draws the tensile fiber portion 35*b* of the contraction wire onto the drum 96. As mentioned above, the stops 146 formed in the channel 144 in which the tab 142 travels limit the rotation of the dial 90. Thus, the stops 146 effectively limits the travel of the contraction wire 35 by which a user can actuate by means of the dial so as to prevent the user from damaging the contraction wire, including over-rotating and breakage.

It is understood that various factors and parameters within the assemblies 80 and 80' can be varied to generate the desirable amount of frictional torque to render the assembly self-holding, including the plurality and combination of rotating and nonrotating washers, the size (or contact surface area) of the washers and their relative positioning (or "stacking order") on the spool. Moreover, these factors and parameters also affect the height or "profile" of the assemblies especially that of the user interface dial so that the present invention is not limited to the disclosed embodiment. It is also understood that any of the foregoing factors and parameters can affect the amount of uniform static and/or dynamic friction torque generated to provide a self-locking dial. Furthermore, consideration is given to space constraints inside the control handle and profile concerns outside the control handle. By increasing the compression of a single washer stack, the static and dynamic friction coefficients diverge greatly as the contact pressure between the washers increase, thus providing a more "jerky" feeling control dial. To that end, the static and dynamic friction coefficients between washers must be similar to each other for smooth dial operation. It is further understood that holding torque is determined by axial compression forces, friction coefficients and the inner and outer diameters of the washers. Thus, a variety of combinations of washers can be used.

In use, a suitable guiding sheath is inserted into the patient with its distal end positioned at a desired mapping location. An example of a suitable guiding sheath for use in connection with the present invention is the Preface™ Braiding Guiding Sheath, commercially available from Biosense Webster, Inc. (Diamond Bar, Calif.). The distal end of the sheath is guided into one of the chamber, for example, the atria. A catheter in accordance with the present invention is fed through the guiding sheath until its distal end extends out of the distal end of the guiding sheath. As the catheter is fed through the guiding sheath, the distal assembly 17 is straightened to fit through the sheath. Once the distal end of the catheter is positioned at the desired location, the guiding sheath is pulled proximally, allowing the deflectable intermediate section 14 and distal assembly 17 to extend outside the sheath, and the distal assembly 17 returns to its original shape due to its shape-memory.

By manipulating and rotating the deflection dial 50 to deflect the intermediate section 14, the distal assembly 17 is then inserted into a pulmonary vein or other tubular region (such as the superior vena cava, or inferior vena cava) so that the outer circumference of the generally circular main region 39 of the assembly 17 is in contact with a circumference inside the tubular region. Turning the deflection dial 50 in one direction deflects the intermediate section 14 to that direction. Turning the deflection 50 in the opposite direction deflects the intermediate section 14 to that opposite direction. Tension of the deflection dial 50 is adjusted by manipulating and rotating a tension dial 51. Turning the dial 51 in one direction increases the tension. Turning the dial 51 in the opposition direction decreases the tension.

The circular arrangement of the electrodes on the generally circular portion 39 permits measurement of the electrical activity at that circumference of the tubular structure so that ectopic beats between the electrodes can be identified. The size of the generally circular main region 39 permits measurement of electrical activity along a diameter of a pulmonary vein or other tubular structure of or near the heart because the circular main region has a diameter generally corresponding to that of a pulmonary vein or other tubular structure. By manipulating the dial 90, the assembly 17, in particular, the generally circular main region 39, is adjusted to fit the pulmonary vein or other tubular structure. In the disclosed embodiment, by rotating the dial in one direction, the contraction wire 35 is drawn proximally to tighten and decrease the diameter of the generally circular region 39. By rotating the dial in the other direction, the contraction wire 35 is released and returned to its prior diameter. Preferably at least about 50%, more preferably at least about 70%, and still more preferably at least about 80% of the circumference of the generally circular main region is in contact with a circumference inside the tubular region.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. For example, the catheter can be adapted such that the third puller wire advances and retracts another component such as a guide wire or a needle. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A control handle for a medical device having an elongated body, a distal assembly distal the elongated body, the distal assembly having an adjustable configuration, the medical device further comprising a puller member extending through the elongated body and the distal assembly, the control handle comprising:
   a housing having an outer surface formed with a channel;
   an actuator assembly comprising:
      a user interface rotational dial including a rib;
      a spool having a shaft body inserted through a through-hole in the housing, the spool having a drum on which the puller member is wound;
      a detent washer mounted on the shaft body, the detent washer having a notch disposed about the rib of the user interface rotational dial, the detent washer having a tab that rides in the channel to guide movement of the detent washer;
      at least one friction-inducing washer mounted on the shaft body; and
      a fastener mounted on the shaft body adapted to generate a compression load on the friction-inducing washer.

2. A control handle of claim 1, wherein the drum is inside the control handle housing.

3. A control handle of claim 1, wherein the detent washer is outside the control handle housing.

4. A control handle of claim 1, wherein the at least one friction-inducing washer is outside the control handle housing.

5. A control handle of claim 1, wherein the actuator assembly further comprises an additional washer mounted on the shaft body inside of the control handle housing, the additional washer in friction-inducing contact with a rim of the drum, the additional washer being locked against rotation relative to the rim.

6. A control handle of claim 1, wherein the channel has a circular form that generally surrounds the through-hole in the control handle housing.

7. A control handle of claim 1, wherein the channel has a stop to limit movement of the tab in the channel.

8. A control handle of claim 1, wherein the actuator assembly further comprises an additional washer mounted on the shaft body in friction-inducing contact with the detent washer, the additional washer being locked against rotation relative to the shaft body.

9. A control handle of claim 1, wherein the fastener is a nut threaded onto the shaft body.

10. A control handle of claim 1, wherein the actuator assembly further comprises an anchor, a proximal end of the puller member being attached to the anchor.

11. A catheter comprising:
    an elongated body;
    a distal assembly having an adjustable configuration;
    a puller member extending through the elongated body and the distal assembly; and
    a control handle comprising:
       a housing having an outer surface formed with a channel;
       an actuator assembly comprising:
          a user interface rotational dial including a rib;
          a spool having a shaft body inserted through a through-hole in the housing, the spool having a drum on which the puller member is wound;
          a detent washer mounted on the shaft body, the detent washer having a notch disposed about the rib of the user interface rotational dial, the detent washer having a tab that rides in the channel to guide movement of the detent washer;
          at least one friction-inducing washer mounted on the shaft body; and
          a fastener mounted on the shaft body adapted to generate a compression load on the friction-inducing washer.

12. A catheter of claim 11, further comprising a pair of puller members extending from the control handle to at or near a distal end of the elongated body, wherein the control handle further comprises a deflection assembly adapted to act on the pair of puller members.

13. A catheter of claim 11, wherein the distal assembly has a generally circular distal portion and a generally straight proximal portion, wherein adjustment of the puller member varies the generally circular distal portion.

14. A control handle of claim 11, wherein the actuator assembly further comprises an additional washer mounted on the shaft body inside of the control handle housing, the additional washer in friction-inducing contact with a rim of the drum, the second additional washer being locked against rotation relative to the rim.

15. A control handle of claim 11, wherein the channel has a circular form that generally surrounds the through-hole in the control handle housing.

16. A control handle of claim 11, wherein the channel has a stop to limit movement of the tab in the channel.

17. A control handle of claim 11, wherein the actuator assembly further comprises an additional washer mounted on the shaft body in friction-inducing contact with the detent washer, the additional washer being locked against rotation relative to the shaft body.

18. A control handle of claim 11, wherein the fastener is a nut threaded onto the shaft body.

19. A control handle of claim 11, wherein the actuator assembly further comprises an anchor, a proximal end of the puller member being attached to the anchor.

20. A control handle of claim 11, wherein the actuator assembly further comprises a bushing lining the through-hole in the control handle housing.

\* \* \* \* \*